United States Patent [19]

Hagan et al.

[11] Patent Number: 5,360,820
[45] Date of Patent: Nov. 1, 1994

[54] MEDICAL USE FOR TACHYKININ ANTAGONISTS

[75] Inventors: Russell M. Hagan; Keith T. Bunce; Alan Naylor; Mark Ladlow, all of Ware, Great Britain; Andrew B. McElroy, Research Triangle Park, N.C.; Andrew R. Whittington; Barry A. Coomber, both of Greenford, Great Britain

[73] Assignee: Glaxo Group Limited, London, United Kingdom

[21] Appl. No.: 946,635

[22] Filed: Sep. 18, 1992

[30] Foreign Application Priority Data

Sep. 20, 1991 [GB] United Kingdom ............... 9120172
Feb. 11, 1992 [GB] United Kingdom ............... 9202839
Feb. 27, 1992 [GB] United Kingdom ............... 9204151

[51] Int. Cl.5 .................. A61K 31/20; A61K 31/55; A61K 31/135; A61K 31/19
[52] U.S. Cl. ............... 514/559; 514/872; 514/561; 514/213; 514/214; 514/221; 514/568; 514/569; 514/648; 514/649; 514/650; 514/654; 514/322; 514/317
[58] Field of Search ............ 514/559, 322, 317, 561, 514/213, 214, 221, 568, 569, 648, 649, 650, 654, 322, 317, 872

[56] References Cited

U.S. PATENT DOCUMENTS

| 4,031,226 | 6/1977 | Soudijn et al. | 424/267 |
| 4,066,772 | 1/1978 | Vandenberk et al. | 424/267 |
| 4,126,687 | 11/1978 | Vandenberk et al. | 424/267 |
| 4,126,688 | 11/1978 | Vandenberk et al. | 424/267 |
| 4,175,129 | 11/1979 | Vandenberk et al. | 424/267 |
| 5,102,667 | 4/1992 | Dubruoequ et al. | 424/489 |

FOREIGN PATENT DOCUMENTS

| 1123088 | 8/1988 | Australia . |
| 0429366 | 5/1991 | European Pat. Off. . |
| 0436334 | 7/1991 | European Pat. Off. . |
| 0499313 | 8/1992 | European Pat. Off. . |
| WO 90/05729 | 5/1990 | WIPO . |

OTHER PUBLICATIONS

Newton et al., *J. Comp. Neurol.*, 234, 87–104, 1985.
Lesley, *Neurochem. Int.*, 7, 191–211, 1985.
Andrews et al., *TIPS*, 9, 334–341, Sep. 1988.
Carpenter et al., *Cell. and Mol. Neurobiol.*, 3, 113,126, 1983.
Carpenter et al., *Fed. Prod. Am. Soc. Exp. Biol.*, 43, 2952–2954, Dec. 1984.
Saffroy et al., *Peptides*, 9, 227–241, 1988.

Primary Examiner—Marianne M. Cintins
Assistant Examiner—T. J. Criares
Attorney, Agent, or Firm—Bacon & Thomas

[57] ABSTRACT

The present invention relates to the use of tachykinin antagonists, including substance P antagonists and other neurokinin antagonists, in the treatment of emesis. Also described are novel tachykinin antagonists of formula (I), processes for their preparation, pharmaceutical compositions containing them and their medical use.

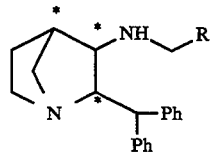

(I)

wherein
R represents the ring A

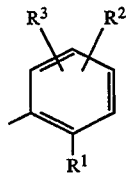

or 2-pyridinyl or 2-pyridinyl-N-oxide;
$R^1$ is selected from halogen atoms and $C_{1-4}$alkyl, $C_{1-4}$alkoxy, trifluoromethyl, and $S(O)_nC_{1-4}$alkyl groups;
$R^2$ and $R^3$, which may be the same or different, each independently are selected from hydrogen and halogen atoms and $C_{1-4}$alkyl, $C_{1-4}$alkoxy, trifluoromethyl and cyano groups;
n represents zero, 1 or 2;
and pharmaceutically acceptable salts and solvates thereof.

9 Claims, No Drawings

MEDICAL USE FOR TACHYKININ ANTAGONISTS

The present invention relates to the use of tachykinin antagonists, including substance P antagonists and other neurokinin antagonists, in the treatment of emesis. Also described are novel tachykinin antagonists, processes for their preparation, pharmaceutical compositions containing them and their medical use.

Tachykinin antagonists are known to be useful in the treatment of a variety of disorders including pain, inflammatory diseases, allergic disorders, CNS disorders, skin disorders, cough and gastrointestinal disorders such as ulcerative colitis and Crohn's disease.

It has now been found that tachykinin antagonists, including substance P antagonists and other neurokinin antagonists, are useful in the treatment of emesis.

The invention accordingly provides, in a first aspect, the novel use of tachykinin antagonists, including substance P antagonists and other neurokinin antagonists, in the treatment of emesis.

There is also provided as a further aspect of the invention the use of tachykinin antagonists, including substance P antagonists and other neurokinin antagonists, in the preparation of a medicament for use in the treatment of emesis.

In an alternative or further aspect there is provided a method for the treatment of a mammal, including man, suffering from or susceptible to emesis, comprising administration of an effective amount of a tachykinin antagonist, including substance P antagonists and other neurokinin antagonists.

It will be appreciated that reference to treatment is intended to include prophylaxis as well as the alleviation of established symptoms.

Tachykinin antagonists, including substance P antagonists and other neurokinin antagonists, have been shown to have anti-emetic activity as indicated by for example their ability to inhibit cisplatin-induced emesis in the ferret.

The treatment of emesis mentioned hereinbefore includes the treatment of nausea, retching and vomiting. Emesis includes acute emesis, delayed emesis and anticipatory emesis. Tachykinin antagonists, including substance P antagonists and other neurokinin antagonists, are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; antimetabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis; pregnancy; vestibular disorders, such as motion sickness; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); and opioid analgesics, such as morphine.

Tachykinin antagonists acting at NK$_1$ receptors have been found to be particularly useful in the treatment of emesis.

In a preferred aspect therefore the invention provides the use of an NK$_1$ receptor antagonist in the treatment of emesis.

Specific tachykinin antagonists for use in the present invention include those generically and specifically disclosed in the following patent specifications which disclosures are incorporated herein by reference:

EP 0327009;
WO 91/12266;
EP 0284942;
GB 2216529;
U.S. Pat. No. 4,839,465;
WO 91/02745
EP 0484719;
WO 91/18016;
EP 0482539;
EP 0446706

Particularly preferred are the tachykinin antagonists disclosed in:
EP 0360390 in particular:
N-[N$^1$-[L-pyroglutamyl-L-alanyl-L-aspartyl-L-prolyl-L-asparaginyl-L-lysyl-L-phenylalanyl-L-tyrosyl]-4-methyl-1-oxo-2S-(6-oxo-5S-1,7diazaspiro[4.4.]nonan-7-yl)pentyl]-L-tryptophanamide and
N-[N$^1$-[L-arginyl-L-prolyl-L-lysyl-L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)-pentyl]-L-tryptophanamide;
WO 90/05525
WO 90/05729 i.e. quinuclidine derivatives of the formulae:

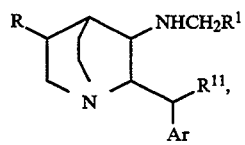

A

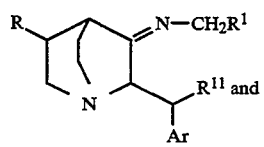

B

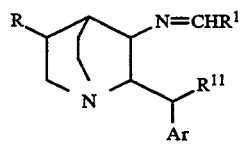

C including the pharmaceutically acceptable salts thereof; wherein Ar is thienyl, phenyl, fluorophenyl, chlorophenyl or bromophenyl; R is hydrogen or alkyl having from one to four carbon atoms; R$^1$ is cycloalkyl having from five to seven carbon atoms, norbornyl, pyrrolyl, 2,3-dihydrobenzofuranyl, thienyl, alkoxythienyl having from one to three carbon atoms in the alkoxy moiety, pyridyl, hydroxypyridyl, quinolinyl, indolyl, naphthyl, alkoxynaphthyl having from one to three carbon atoms in the alkoxy moiety, biphenyl 2,3-methylenedioxyphenyl, or phenyl optionally substituted with up to two substituents selected from cyano, nitro, amino, N-monoalkylamino having from one to three carbon atoms in the alkyl moiety, fluorine, chlorine, bromine, trifluoromethyl, alkyl having from one to three carbons, alkoxy having from one to three carbon atoms, allyloxy, hydroxy, carboxy, alkoxycarbonylbenzyloxy having from one to three carbon atoms in the alkoxy moiety, carboxamido or N,N-dialkylcarboxamido having from one to three carbon atoms in the alkyl moiety; and $R^{11}$ is branched chain alkyl having from three to four carbon atoms, branched chain alkenyl having from five to six carbon atoms, cycloalkyl having from five to seven carbon atoms, furyl, thienyl, pyridyl, indolyl, biphenyl, or phenyl optionally substituted with up to two substituents selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety or benzyloxycarbonyl, with the proviso that said $R^{11}$ is always other than unsubstituted phenyl, fluorophenyl, chlorophenyl, bromophenyl or alkylphenyl when said $R^1$ is unsubstituted phenyl, pyrrolyl or thienyl and Ar is other than thienyl;

for example cis-3-[(2-methoxyphenyl)methylamino]-2-benzhydrylquinuclidine;

WO 91/18899 i.e. compounds of the formula:

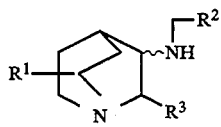

D wherein $R^1$ is hydrogen or $(C_1-C_6)$alkyl; $R^2$ is phenyl, pyridyl, thienyl or furyl, and $R^2$ may optionally be substituted with from one to three substituents independently selected from $(C_1-C_4)$alkyl, $(C_1-C_4)$alkoxy, chloro, fluoro, bromo, iodo and trifluoromethyl; $R^3$ is phenyl, naphthyl, pyridyl, thienyl or furyl, and $R^3$ may optionally be substituted with one to three substituents independently selected from $(C_1-C_4)$alkyl, $(C_1-C_4)$alkoxy, chloro, fluoro, bromo, iodo and trifluoromethyl; and the pharmaceutically acceptable salts of such compounds;

WO 92/01688 i.e. compounds of the formula:

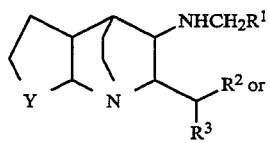

E

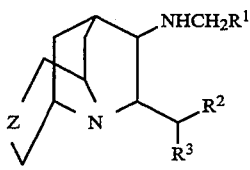

F

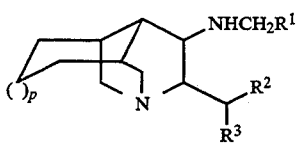

G wherein Y is $(CH_2)_m$ wherein m is an integer from one to three, or Y is a group of the formula

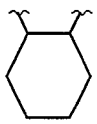

P is an integer from zero to one;

Z is oxygen, sulfur, amino, N—$(C_1-C_3)$ alkylamino or —$(CH_2)_n$— and n is zero, one or two;

Ar is thienyl, phenyl, fluorophenyl, chlorophenyl or bromophenyl; $R^1$ is cycloalkyl having from five to seven carbon atoms, pyrrolyl, thienyl, pyridyl, phenyl or substituted phenyl, wherein said substituted phenyl is substituted with one to three substituents selected from fluorine, chlorine, bromine, trifluoromethyl, alkyl having from one to three carbon atoms, alkoxy having from one to three carbon atoms, carboxy, alkoxycarbonyl having from one to three carbons in the alkoxy moiety and benzyloxycarbonyl; and $R^2$ is furyl, thienyl, pyridyl, indolyl, biphenyl, phenyl or substituted phenyl, wherein said substituted phenyl is substituted with one or two substituents selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl, or a pharmaceutically acceptable salt thereof; for example 8-benzhydryl-n-phenylmethyl]-9-azatricyclo[4.3.-1.0$^{4.9}$]decan-7-amine;

8-benzhydryl-n-[(2-chlorophenyl)methyl]-9-azatricyclo[4.3.-1.0$^{4.9}$]decan-7-amine;

8-benzhydryl-n-[(4-trifluoromethylphenyl)methyl]-9-azatricyclo[4.3.-1.0$^{4.9}$]decan-7-amine; or 8-benzhydryl-n-[(2-methoxyphenyl)methyl]-9-azatricyclo[4.3.-4.3.-1.0$^{4.9}$]decan-7-amine.

WO 92/06079 i.e. compounds of the formula:

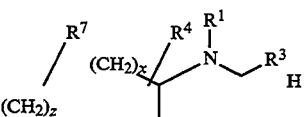

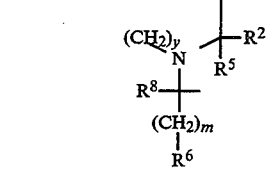

wherein

X is an integer from zero to four;

Y is an integer from zero to four;

z is an integer from one to six;

the ring containing $(CH_2)_z$ may contain from zero to three double bonds, and one of the carbons of $(CH_2)_z$ may optionally be replaced by oxygen, sulfur or nitrogen;

m is an integer from zero to twelve, and any one of the carbon-carbon single bonds of $(CH_2)_m$ may optionally be replaced by a carbon-carbon double or triple bond and any one of the carbon atoms of said $(CH_2)_m$ may optionally be substituted with $R^8$;

$R^1$ is hydrogen or $(C_1-C_6)$alkyl optionally substituted with hydroxy, alkoxy or fluoro;

$R^2$ is a radical selected from hydrogen, ($C_1$-$C_6$) straight or branched alkyl, ($C_3$-$C_7$) cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl ($C_2$-$C_6$) alkyl, benzhydryl and benzyl, wherein each of said aryl and heteroaryl groups and the phenyl moieties of said benzyl, phenyl ($C_2$-$C_6$) alkyl and benzhydryl groups may optionally be substituted with one or more substituents independently selected from halo, nitro, ($C_1$-$C_6$)alkyl, ($C_1$-$C_6$) alkoxy, trifluoromethyl, amino, ($C_1$-$C_6$)-alkylamino, ($C_1$-$C_6$)alkyl-O—C(O), ($C_1$-$C_6$)alkyl-O—C(O)($C_1$-$C_6$)alkyl, ($C_1$-$C_6$)alkyl-$CO_2$—, ($C_1$-$C_6$)alkyl-C(O)— ($C_1$-$C_6$)alkyl-O—, ($C_1$-$C_6$)alkyl-C(O)—, ($C_1$-$C_6$)alkyl-C(O)-($C_1$-$C_6$)alkyl—, di-($C_1$-$C_6$) alkylamino, —CONH-($C_1$-$C_6$)alkyl, ($C_1$-$C_6$)alkyl-CONH— ($C_1$-$C_6$)alkyl, —NHC(O)H and —NHC(O)(-$C_1$-$C_6$)alkyl;

$R^5$ is hydrogen or ($C_1$-$C_6$)alkyl;

or $R^2$ and $R^5$, together with the carbon to which they are attached, form a saturated carbocyclic ring having from 3 to 7 carbon atoms, wherein one of said carbon atoms may optionally be replaced by oxygen, nitrogen or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; or cycloalkyl having from three to seven carbon atoms, wherein one of said carbon atoms may optionally be replaced by nitrogen, oxygen or sulfur; wherein each of said aryl and heteroaryl groups may optionally be substituted with one or more substitutents and said ($C_3$-$C_7$) cycloalkyl may optionally be substituted with one or two substituents, said substituents being independently selected from halo, nitro, ($C_1$-$C_6$) alkyl, ($C_1$-$C_6$) alkoxy, trifluoromethyl, amino, phenyl, ($C_1$-$C_6$)alkylamino, —CONH-($C_1$-$C_6$)alkyl, ($C_1$-$C_6$)alkyl-CONH-($C_1$-$C_6$)alkyl, —NHC(O)H and —NHC(O)-($C_1$-$C_6$) alkyl;

$R^4$ may be attached to any atom of the nitrogen containing ring having an available bonding site and $R^7$ may be attached to any atom of the ($CH_2$)$_z$ containing ring having an available bonding site;

$R^4$, $R^6$, $R^7$ and $R^8$ are each independently selected from hydrogen, hydroxy, halo, amino, carboxy, carboxyalkyl, ($C_1$-$C_6$) alkylamino, di-($C_1$-$C_6$)alkylamino, ($C_1$-$C_6$)alkoxy, ($C_1$-$C_6$)alkyl-O—C(O)—, ($C_1$-$C_6$)alkyl-O—C(O)-($C_1$-$C_6$)alkyl, ($C_1$-$C_6$)alkyl-$CO_2$, ($C_1$-$C_6$)alkyl-C(O)-($C_1$-$C_6$)alkyl-O-($C_1$-$C_6$)alkyl-C(O)—, ($C_1$-$C_6$)alkyl-C(O)($C_1$-$C_6$)alkyl, and the radicals set forth in the definition of $R^2$, with the proviso that (a) when m is O, $R^8$ is absent, (b) neither $R^4$, $R^6$, $R^7$ nor $R^8$ can form, together with the carbon to which it is attached, a ring with $R^5$, and (c) $R^4$ and $R^7$ can not be attached to the same carbon atom;

or a pharmaceutically acceptable salt thereof; for example [1α, 3α, 4α, 5α]-4-(2-methoxybenzyl)amino-3-phenyl-2-azabicyclo[3.3.0]octane;
4-(2-methoxybenzyl)amino-3-phenyl-2-azabicyclo[4.4.0]decane; or
4-(2-methoxybenzyl)amino-4-benzhydryl-3-azabicyclo[4.1.0]heptane.

EP 0429366 i.e. isoindoline derivatives of the formula:

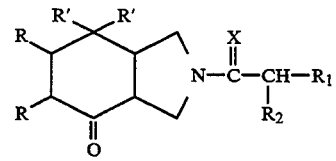

in the (3aR, 7aR) and (3aRS, 7aRS) forms, and mixtures and salts thereof where

R represents hydrogen, or together R and R form a bond;

R' are identical and represent phenyl, optionally substituted by halogen or methyl in position 2 or 3;

X represents O, S or $NR^3$;

$R_3$ represents hydrogen, $C_{1-12}$alkyl (optionally substituted by one or more carboxy, dialkylamino, acylamino, alkoxycarbonyl, alkoxycarbonylamino, carbamoyl, alkylcarbamoyl, dialkylcarbamoyl (where the alkyl portions of these radicals may contain a dialkylamino or phenyl substituent), phenyl (optionally substituted by halogen, alkyl, alkoxy or dialkylamino), naphthyl, thienyl, furyl, pyridyl or imidazolyl); or dialkylamino;

$R_1$ represents phenyl (optionally substituted by 1 or more halogen, OH, alkyl (optionally substituted by halogen, amino, alkylamino or dialkylamino), alkoxy or alkylthio (optionally substituted by OH or dialkylamino of which the alkyl portions may form a 5- to 6-membered heterocycle which can contain another O, S or N heteroatom), or substituted by amino, alkylamino or dialkylamino);

or $R_1$ is a cyclohexadienyl, naphthyl or (un)saturated 5-9C mono or polycyclic heterocyclyl having one or more O, N or S heteroatoms;

$R_2$ represents H, halogen, OH, alkyl, aminoalkyl, alkylaminoalkyl, dialkylaminoalkyl, alkoxy, alkylthio, acyloxy, carboxy, alkoxycarbonyl, dialkylaminoalkoxycarbonyl, benxyloxycarbonyl, amino, acylamino or alkoxycarbonylamino; the various alkyl and acyl groups being straight or branched and of 1-4C atoms;

for example

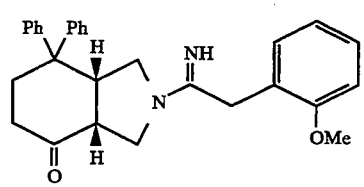

EP 0428434 i.e. 1,4-diaralkylpiperidine and piperazine derivatives of the formula:

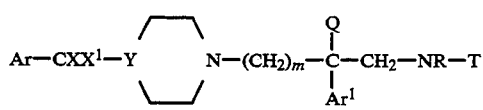

where
m=1–3;
Ar, $Ar^1$ represents thienyl; phenyl optionally mono- or disubstituted by halogen, 1-3C alkyl, $CF_3$, 1-3C alkoxy, OH or methylenedioxy; or imidazolyl; or $Ar^1$ may also be benzothienyl optionally substituted by halogen; naphthyl optionally substituted by halogen; biphenylyl; or indolyl optionally substituted by benzyl;
$X^1$ represents hydrogen or OH;

Y represents N or $CX^{11}$;
X and $X^{11}$ represent hydrogen; or $X^1$ or $X^{11}$ is a bond; or
X and $X^1$ represent O or NO( $CH_2$)pAm;
p represents 2 or 3;
Am represents di(1–4Calkyl)amino;
Q represents hydrogen, 1–4Calkyl or ($CH_2$)qAm;
q represents 2 or 3;
Am represents piperidino, 4-benzylpiperidino or di(1–4-Calkyl)amino;
R represents hydrogen, methyl or $(CH_2)_nL$;
L represents hydrogen or $NH_2$;
n represents 2–6;
T represents COM, COOM, CONHM or CSNHM;
M represents hydrogen, 1–6C alkyl, phenyl(1–3C)alkyl (optionally ring-substituted by halogen, OH, 1–4C alkoxy or 1–4C alkyl), pyridyl(1–3C)alkyl, naphthyl(1–3-C)alkyl, pyridylthio(1–3C)alkyl, styryl, 1-methyl-2-imidazolylthio(1–3C) alkyl, 1-oxo-3-phenyl-2indanyl or optionally substituted aryl or heteroaryl; and optical isomers and acid addition salts thereof;

EP 0336230 i.e. compounds of the formula:

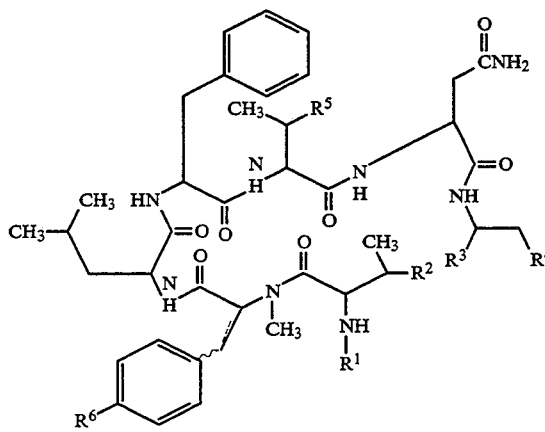

wherein
$R^1$ is hydrogen or an acyl group;
$R^2$ is hydroxy and
$R^3$ is carboxy or protected carboxy, or
$R^2$ and $R^3$ are linked together to represent a group of the formula: —O—C(O);
$R^4$ is hydroxy or protected hydroxy;
$R^5$ is hydroxy or protected hydroxy;
$R^6$ is hydroxy, protected hydroxy or lower alkoxy; and  is a single bond or a double bond;
for example

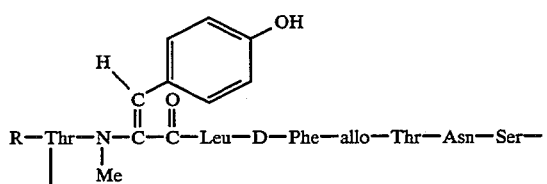

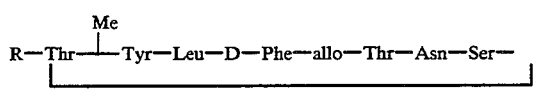

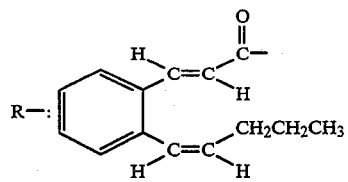

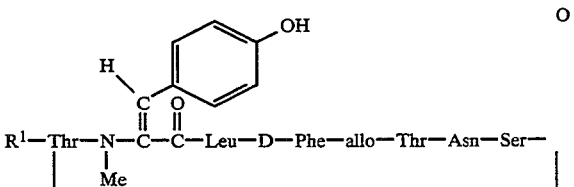

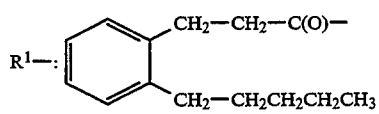

EP 0333174 i.e. compounds of the formula $R^1$-A-D-Trp($R^2$)-Phe-$R^3$  P wherein $R^1$ is hydrogen or an amino protective group;

$R^2$ is hydrogen, an amino protective group, carbamoyl(-lower) alkyl, carboxy (lower) alkyl or protected carboxy(lower) alkyl;

$R^3$ is ar(lower)aklyl;

a group of the formula $$-N\begin{matrix}R^4\\R^5\end{matrix}$$

wherein $R^4$ and $R^5$ are each hydrogen, aryl or lower alkyl which may have suitable substituent(s) or $R^4$ and $R^5$ are linked together to form benzene-condensed lower alkylene, or a group of the formula:

—$OR^6$ wherein $R^6$ is hydrogen, aryl or lower alkyl which may have suitable substituent(s), and A is a single bond or one or two amino acid(s) residue, provided that when A is one amino acid residue of -D-Trp-, then $R^4$ is not hydrogen;

and a pharmaceutically acceptable salt thereof
for example

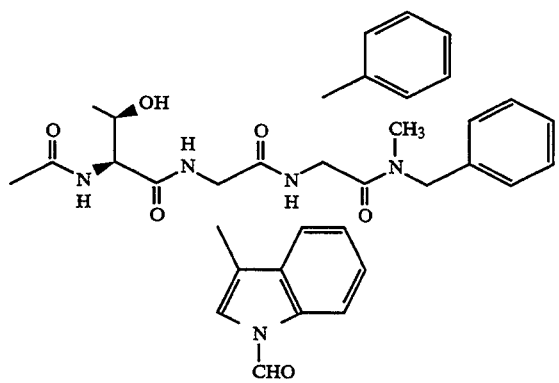

EP 0394989 i.e. compounds of the formula

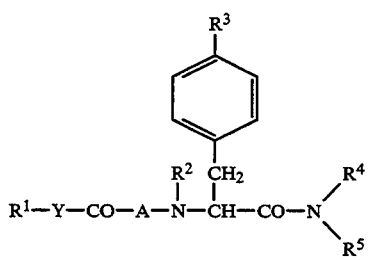

wherein R¹ is lower alkyl, aryl, arylamino, pyridyl, pyrrolyl, pyrazolopyridyl, quinolyl, or a group of the formula:

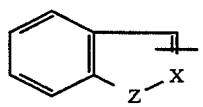

wherein the symbol of a line and dotted line is a single bond or double bond,
X is CH or N, and
Z is O, S or NH, each of which may have suitable substituents(s);
R² is hydrogen or lower alkyl;
R³ is hydrogen or hydroxy;
R⁴ is lower alkyl which may have suitable substituent(s), and
R⁵ is ar(lower)alkyl which may have suitable substituent(s) or pyridyl(lower)alkyl, or
R⁴ and R⁵ are linked together to form benzene-condensed lower alkylene;
A is an amino acid residue excepting D-Trp, which may have suitable substituent(s); and
Y is a bond, lower alkylene or lower alkenylene;
for example

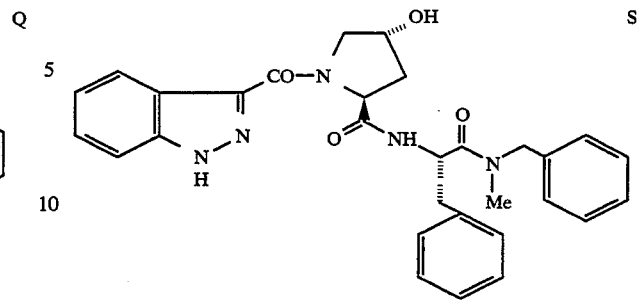

EP 0443132 i.e. compounds of the formula:

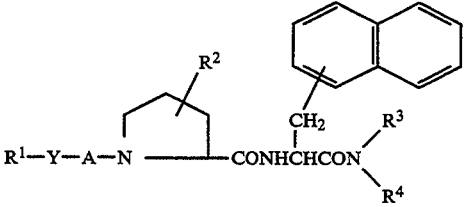

wherein R¹ is aryl, or a group of the formula:

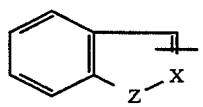

wherein
X is CH or N, and
Z is O or N—R⁵, in which R⁵ is hydrogen or lower alkyl,
R² is hydroxy or lower alkoxy,
R³ is hydrogen lower alkyl which may have suitable substituent(s),
R⁴ is ar(lower)alkyl which may have suitable substituent(s),
A is carbonyl or sulfonyl, and
Y is bond, or lower alkenylene;
for example

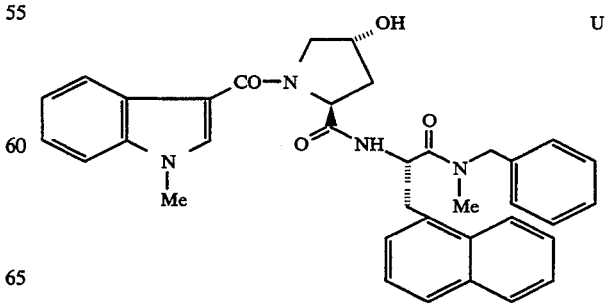

EP0499313 i.e. compounds of the formula

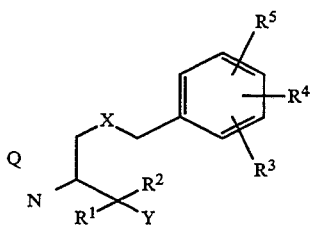

wherein

Q is the residue of an optionally substituted azabicyclic ring system;

X represents oxa or thia;

Y represents H or hydroxy;

$R^1$ and $R^2$ independently represent phenyl or thienyl, either of which groups may be optionally substituted by halo or trifluoromethyl;

$R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, $-OR^a$, $SCH_3$, $SOCH_3$, $SO_2CH_3$, $-NR^aR^b$, $NR^aCOR^b$, $NR^aCO_2R^b$, $-CO_2R^a$ or $-CONR^aR^b$; and $R^a$ and $R^b$ independently represent H, $C_{1-6}$alkyl, phenyl or trifluoromethyl; or a salt or prodrug thereof;

for example cis-(2S,3S)-3-[3,5-bis(trifluoromethyl)benzyloxy]-2-(diphenylmethyl)-1-azabicyclo]2.2.2]octane.

EP 0436334 i.e. compounds of the formula:

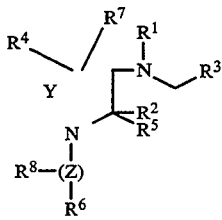

wherein Y is $(CH_2)_n$ wherein n is an integer from 1 to 4, and wherein any one of the carbon-carbon single bonds in said $(CH_2)_n$ may optionally be replaced by a carbon-carbon double bond, and wherein any one of the carbon atoms of said $(CH_2)_n$ may optionally be substituted with $R^4$ and wherein any one of the carbon atoms of said $(CH_2)_n$ may optionally be substituted with $R^7$;

Z is $(CH_2)_m$ wherein m is an integer from 0 to 6, and wherein any one of the carbon-carbon single bonds of $(CH_2)_m$ may optionally be replaced by a carbon-carbon double bond or carbon-carbon triple bond, and any one of the carbon atoms of said $(CH_2)_m$ may optionally be substituted with $R^8$;

$R^1$ is hydrogen or $(C_1-C_8)$ alkyl optionally substituted with hydroxy, $(C_1-C_4)$alkoxy or fluoro;

$R^2$ is a radical selected from hydrogen, $(C_1-C_6)$ straight or branched alkyl, $(C_3-C_7)$ cycloalkyl wherein one of the $CH_2$ groups in said cycloalkyl may optionally be replaced by NH, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$-alkyl, benzhydryl and benzyl, wherein each of said aryl and heteroaryl groups and the phenyl moieties of said benzyl, phenyl$(C_2-C_6)$-alkyl and benzhydryl may optionally be substituted with one or more substituents independently selected from halo, nitro, $(C_1-C_6)$ alkyl, $(C_1-C_6)$ alkoxy, trifluoromethyl, amino, $(C_1-C_6)$-alkylamino, $(C_1-C_6)$alkyl-O—C(O)—, $(C_1-C_6)$alkyl-O—C(O)-$(C_1-C_6)$alkyl, $(C_1-C_6)$alkyl-C(O)—O—, $(C_1-C_6)$alkyl-C(O)—, $(C_1-C_6)$alkyl-O—, $(C_1-C_6)$alkyl-C(O)—, $(C_1-C_6)$alkyl-C(O)-$(C_1-C_6)$alkyl-, di-$(C_1-C_6)$alkylamino, —CONH-$(C_{1-6})$alkyl, $(C_1-C_6)$-alkyl-CONH-$(C_1-C_6)$alkyl, NHC(O)H and —NHC(O)-$(C_1-C_6)$ alkyl;

and wherein one of the phenyl moieties of said benzhydryl may optionally be replaced by naphthyl, thienyl, furyl or pyridyl;

$R^5$ is hydrogen, phenyl or $(C_1-C_6)$ alkyl;

or $R^2$ and $R^5$, together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl; tetrazolyl and quinolyl; and cycloalkyl having 3 to 7 carbon atoms wherein one of the $(CH_2)$ groups in said cycloalkyl may optionally be replaced by NH, oxygen or sulfur;

wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl, $(C_1-C_6)$ alkoxy, trifluoromethyl, amino, $(C_1-C_6)$ alkylamino, —CONH-$(C_1-C_6)$alkyl, $(C_1-C_6)$alkyl-C(O)—NH-$(C_1-C_6)$alkyl, —NHC(O)H and —NH-C(O)-$(C_1-C_6)$alkyl; and $R^4$ and $R^7$ are each independently selected from hydroxy, hydrogen, halo, amino, oxo, cyano, methylene, hydroxymethyl, halomethyl, $(C_1-C_6)$alkylamino, di-$(C_1-C_6)$alkylamino, $(C_1-C_6)$ alkoxy, $(C_1-C_6)$alkyl-O-C(O)—, $(C_1-C_6)$alkyl-O—C(O)-$(C_1-C_6)$alkyl, $(C_1-C_6)$alkyl-C(O), $(C_1-C_6)$alkyl-C—(O)-$(C_1-C_6)$alkyl-O, $(C_1-C_6)$alkyl-C(O), $(C_1-C_6)$alkyl-C(O)-$(C_1-C_6)$alkyl-, and the radicals set forth in the definition of $R^2$, $R^6$ is NHC(O)$R^9$, —NHCH$_2R^9$, SO$_2R^9$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $(C_1-C_6)$alkyl, hydrogen, phenyl or phenyl$(C_1-C_6)$alkyl;

with the proviso that (a) when m is 0, $R^8$ is absent, (b) when $R^4$, $R^6$, $R^7$ or $R^8$ is as defined in $R^2$, it cannot form, together with the carbon to which it is attached, a ring with $R^5$, and (C) when $R^4$ and $R^7$ are attached to the same carbon atom, then either each of $R^4$ and $R^7$ is independently selected from hydrogen, fluoro and $(C_1-C_6)$ alkyl, or $R^4$ and $R^7$, together with the carbon to which they are attached, form a $(C_3-C_6)$ saturated carbocyclic ring that forms a spiro compound with the nitrogen-containing ring to which they are attached; and pharmaceutically acceptable acid addition salts thereof;

in particular cis-3-(2-methoxybenzylamino)-2-phenyl piperidine, more particularly the (2S,3S) or (+) enantiomer thereof.

Of the above, the most preferred tachykinin antagonists for use in the present invention are found within WO90/05525, WO90/05729, WO91/18899, WO92/01688, WO92/06079, EPO499313 and, more preferably, EPO436334, i.e. compounds of the formulae A,B,C,D,E,F,G,H,V' and, more preferably, W as defined hereinbefore.

Also preferred for use in the present invention are the compounds of formula (I) defined hereinafter.

The tachykinin antagonists may be administered as the raw chemical but the active ingredients are preferably presented as a pharmaceutical formulation. Suitable pharmaceutical formulations are described in the above referenced patent specifications.

Thus, the tachykinin antagonists may be formulated for oral, buccal, parenteral, depot or rectal administration or in a form suitable for administration by inhalation or insufflation (either through the mouth or nose). Oral and parenteral formulations are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The tachykinin antagonists may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The tachykinin antagonists may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents.

Drops may be formulated with an aqueous or non aqueous base also comprising one or more dispersing agents, stabilising agents, solubilising agents or suspending agents. They may also contain a preservative.

The tachykinin antagonists may also be formulated in rectal compositions such as suppositories or retention enemas, e.g. containing conventional suppository bases such as cocoa butter or other glycerides.

The tachykinin antagonists may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the tachykinin antagonists may be formulated as solutions for administration via a suitable metered or unit dose device or alternatively as a powder mix with a suitable carrier for administration using a suitable delivery device.

Suitable dose ranges are also described in the above referenced patent specifications, that is to say that for use as anti-emetics the compounds may be used at doses appropriate for other conditions for which tachykinin antagonists are known to be useful. It will be appreciated that it may be necessary to make routine variations to the dosage, depending on the age and condition of the patient, and the precise dosage will be ultimately at the discretion of the attendant physician or veterinarian. The dosage will also depend on the route of administration and the particular compound selected. A suitable dose range is for example 0.1 mg/kg to about 400 mg/kg bodyweight per day.

The tachykinin antagonists may, if desired, be administered in combination with one or more other therapeutic agents and formulated for administration by any convenient route in a conventional manner. Appropriate doses will be readily appreciated by those skilled in the art. For example, the tachykinin antagonists may be administered in combination with a systemic anti-inflammatory corticosteroid such as methyl prednisolone or dexamethasone, or a 5HT$_3$ antagonist such as ondansetron, granisetron or metoclopramide.

The present invention also relates to novel compounds which are potent and specific antagonists of tachykinins, including substance P and other neurokinins.

The art relating to tachykinin antagonists is discussed hereinbefore, see for example WO90/05729 relating to quinuclidine derivatives and EP 0436334.

Thus, in a further aspect the present invention provides a 2,2,1-azabicycloheptane derivative of formula (I)

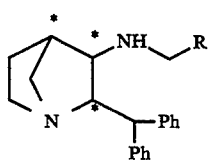

wherein
R represents the ring A

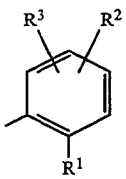

or 2-pyridinyl or 2-pyridinyl-N-oxide;

$R^1$ is selected from halogen atoms and $C_{1-4}$alkyl, $C_{1-4}$alkoxy, trifluoromethyl, and $S(O)_nC_{1-4}$alkyl groups;

$R^2$ and $R^3$, which may be the same or different, each independently are selected from hydrogen and halogen atoms and $C_{1-4}$alkyl, $C_{1-4}$alkoxy, trifluoromethyl and cyano groups;

n represents zero, 1 or 2;

and pharmaceutically acceptable salts and solvates thereof.

Suitable pharmaceutically acceptable salts of the compounds of general formula (I) include acid addition salts formed with pharmaceutically acceptable organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates.

Other acids, such as oxalic, while not in themselves pharmaceutically acceptable, may be useful in the preparation of salts useful as intermediates in obtaining the compounds of formula (I) and their pharmaceutically acceptable acid addition salts.

The solvates may, for example, be hydrates.

It will be appreciated by those skilled in the art that the compounds of formula (I) contain at least three chiral centres (shown as * in formula (I)) and thus exist in the form of four pairs of optical isomers (i.e. enantiomers) and mixtures thereof including racemic mixtures.

For example the compounds of formula (I) may be either cis isomers, as represented by figures (a) and (b), or trans isomers, as represented by figures (c) and (d), or mixtures thereof.

All of the isomers represented by the figures (a) to (d) can exist as one of two enantiomers or as mixtures thereof including racemic mixtures. All such isomers of the compounds of formula (I) and mixtures thereof including racemic mixtures are included within the scope of the invention.

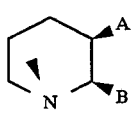

(a)

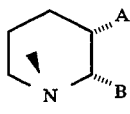

(b)

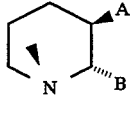

(c)

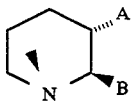

(d)

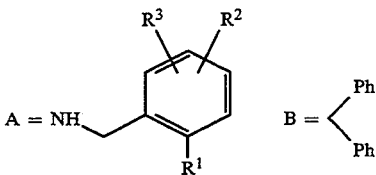

The compound of formula (I) are preferably in the form of their cis isomers (i.e. as represented by figures (a) and (b)).

Referring to the general formula (I), a $C_{1-4}$alkyl group may be a straight chain or branched chain alkyl group, for example, methyl, ethyl, propyl, prop-2-yl, butyl, but-2-yl or 2-methylprop-2-yl. A $C_{1-4}$alkoxy group may be a straight chain or branched chain alkoxy group, for example, methoxy, ethoxy, propoxy, prop-2-oxy, butoxy, but-2-oxy or 2-methylprop-2-oxy.

Referring to the general formula (I), a halogen atom may be, for example, a fluorine, chlorine, bromine or iodine atom.

When R represents the ring A, $R^2$ and $R^3$ may be attached at either the 3-,4-,5- or 6-(e.g. the 3-and 5-) positions of the phenyl ring.

A preferred class of compounds of formula (I) is that in which R represents the ring A and $R^1$ represents a $C_{1-4}$alkoxy(e.g. methoxy) or $S(O)_nC_{1-4}$alkyl group, preferably where n is zero or 1 (e.g. SOMe or SMe). Preferably $R^1$ represents $C_{1-4}$alkoxy (e.g. methoxy).

Another preferred class of compounds of formula (I) is that in which R represents the ring A and $R^2$ and/or $R^3$ represents a hydrogen or a halogen (e.g. fluorine) atom, or a cyano group. Preferably $R^2$ and/or $R^3$ represents a hydrogen or a halogen (e.g. fluorine) atom.

A further preferred class of compounds of formula (I) is that in which R represents the ring A and one of $R^2$ and $R^3$ represents hydrogen and the other represents a hydrogen atom or a halogen (e.g. fluorine) atom preferably at the 5-position of the phenyl ring.

Further preferred are compounds of formula (I) where R represents the ring A where $R^1$ represents $C_{1-4}$alkoxy (e.g. methoxy) or $S(O)_nC_{1-4}$alkyl, preferably where n is zero or 1 (e.g. SOMe or SMe) and one of $R^2$ and $R^3$ represents hydrogen and the other represents a hydrogen or halogen (e.g. fluorine) atom.

Preferred compounds of formula (I) according to the invention are (exo,exo)-2-(Diphenylmethyl)-N-[(2-methoxyphenyl)-methyl]-1-azabicyclo[2.2.1]heptan-3-amine;

(exo,exo)-2-(Diphenylmethyl)-N-[(5-fluoro-2-methoxyphenyl)methyl]-1-azabicyclo[2.2.1]heptan-3-amine;

(endo,endo)-2-(Diphenylmethyl)-N-[(2-methoxyphenyl)methyl]-1-azabicyclo[2.2.1]heptan-3-amine;

(endo,endo)-2-(Diphenylmethyl)-N-[(5-fluoro-2-methoxyphenyl)methyl]-1-azabicyclo[2.2.1]heptan-3-amine;

(endo,endo)-2-(diphenylmethyl)-N-[(2-pyridylmethyl]-1-azabicyclo[2.2.1]heptan-3-amine;

(endo,endo)-2-(diphenylmethyl)-N-[(2-methylthiophenyl)methyl]-1-azabicyclo[2.2.1]heptan-3-amine;

and pharmaceutically acceptable salts and solvates thereof.

The compounds of formula (I) are antagonists of tachykinins, including substance P and other neurokinins both in vitro and in vivo and are thus of use in the treatment of conditions mediated by tachykinins, including substance P and other neurokinins.

In particular the compounds of formula (I) possess $NK_1$-receptor antagonist activity as determined in vitro by their ability to displace $^3H$-substance P in the rabbit cortex using the method of Dam, V. and Quirion, R., *Peptides*, 7, 855-864, (1986) by using rabbit cerebral cortex membranes, and from functional studies in the rabbit thoracic aorta using the method of Brown, J. R. et al, *Tachykinin Antagonists*, Hakanson, R. and Sundler, F. (Eds.) Elsevier:Amsterdam, (1985) pp.305-312.

The compounds of formula (I) have been shown to exhibit substance P antagonist activity in vivo by for example their ability to antagonise substance P methylester-induced bronchoconstriction in the anaesthetised guinea-pig using the method of Hagan et al in *Neuropeptides*, 19, 127-135, (1991) with the antagonists administered intravenously.

The compounds of formula (I) have been shown to have analgesic activity as indicated by for example their ability to inhibit acetic acid-induced abdominal constriction in mice using the method of Collier et al in *Brit. J.Pharmac. Chemother.*, 32, 295-310, (1968).

Also the compounds of formula (I) have been shown to have antiinflammatory activity as indicated by for example their ability to inhibit paw oedema induced by intra-plantar administration of a combination of the $NK_1$ receptor agonist GR73632 and the vasodilator neuropeptide CGRP using the method as described by Beresford, I. J. M. et al in *Brit.J.Pharmacol.*, 102, 360, (1991).

Compounds of formula (I) have been shown to have antipsychotic activity as demonstrated by their ability to antagonise locomotor hyperactivity in mice induced by intra-cerebroventricular injection of the $NK_1$ receptor agonist GR73632 according to the method of Elliott, P. J. et al, *Brit.J.Pharmacol.*, 102, 73, (1991).

The compounds of formula (I) have been shown to have antiemetic activity as indicated by for example their ability to inhibit cisplatin-induced emesis in the ferret using the test method as described hereinbefore.

Compounds of formula (I) are therefore useful as analgesics in particular they are useful in the treatment of traumatic pain such as postoperative pain; menstrual pain; headaches such as migraine and cluster headache; and gastrointestinal pain.

Compounds of formula (I) are also useful as antiinflammatory agents in particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of formula (I) are also useful in the treatment of allergic disorders in particular allergic disorders of the skin such as urticaria, and allergic disorders of the airways such as rhinitis.

Compounds of formula (I) may also be useful in the treatment of CNS disorders in particular psychoses such as schizophrenia, mania, dementia or other cognitive disorders e.g. Alzheimer's disease; anxiety; AIDS related dementia; diabetic neuropathy; multiple sclerosis; depression; Parkinson's disease; and dependency on drugs or substances of abuse; and also the compounds of formula (I) may act as myorelaxants and antispasmodics.

Compounds of formula (I) are also useful in the treatment of emesis, where emesis is as defined hereinbefore. The compounds of formula (I) are useful in the treatment of emesis however induced. For example, emesis may be induced by the emetogens discussed hereinbefore.

Compounds of formula (I) are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose). Suitable pharmaceutical compositions are as described hereinbefore.

A proposed dose of the compounds of formula (I) is 0.1 mg/kg to about 400 mg/kg bodyweight per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

The compounds of formula (I) may, if desired, be administered with one or more therapeutic agents and formulated for administration by any convenient route in a conventional manner. Appropriate doses will be readily appreciated by those skilled in the art. For example, the compounds of formula (I) may be administered in combination with a systematic anti-inflammatory corticosteroid such as methyl prednisolone or dexamethasone, or a 5HT$_3$ antagonist such as ondansetron, granisetron or metoclopramide.

Compounds of formula (I), and salts and solvates thereof, may be prepared by the general methods outlined hereinafter. In the following description, the groups $R^1$ to $R^3$ are as previously defined for compounds of formula (I) unless otherwise stated.

According to a first general process (A), a compound of formula (I) may be prepared by reacting a compound of formula (II):

(II)

with a substituted methylamine of formula (III)

NH$_2$CH$_2$—R     (III)

to form the intermediate imine, which may be isolated if required, followed by reduction of the imine using a suitable metal reducing agent such as a metal hydride, for example a borane hydride, alane hydride or a metal hydride complex like lithium aluminum hydride or sodium borohydride, or an organo-metallic complex such as boranemethyl sulphide, 9-borobicyclononane (9-BBN), triethylsilane, sodium triacetoxyborohydride, sodium cyanoborohydride and the like. Alternatively, catalytic hydrogenation may be used, for example using a platinium catalyst in a suitable solvent e.g. ethanol.

The condensation reaction conveniently takes place in a suitable solvent such as an alcohol (e.g. methanol), an aromatic hydrocarbon (e.g. benzene, toluene or xylene) or a chlorinated hydrocarbon (e.g. dichloromethane or dichloroethane) at a temperature ranging from ambient to the reflux temperature of the reaction mixture. The reaction preferably takes place in the presence of a catalytic amount of a suitable acidic condensing agent such as p-toluenesulphonic acid and/or a dehydrating agent such as molecular sieves.

The reduction step conveniently takes place in a suitable solvent such as acetonitrile, dimethylformamide, benzene, ethers such as diethyl ether, tetrahydrofuran, dioxane and 1,2-dimethoxyethane and alcohols such as ethanol at a temperature ranging from 0° C. to the reflux temperature of the reaction mixture.

Process (A) may also take place in one step without formation of the intermediate imine if the condensation reaction takes place in the presence of sodium cyanoborohydride. Further reduction is therefore unnecessary in this case.

According to a further general process (B), a compound of formula (I) may be prepared by reacting a compound of formula (IV)

(IV)

with a compound of formula (V)

OHC—R     (V)

to form the intermediate imine, which may be isolated if required, followed by reduction. The condensation and reduction steps take place under the conditions as described above for process (A).

Process (B) may also take place in one step as described for process (A).

Compounds of formula (II) may be prepared by reacting the compound of formula (VI)

(VI)

with phenylmagnesium bromide in a Grignard reaction. The reaction conveniently takes place in a suitable solvent such as an ether (e.g. tetrahydrofuran) at a temperature in the range of −10° to 25° C. and optionally in the presence of an agent which promotes 1,4 addition such as a source of Cu(I) ions e.g. copper thiophenolate.

The compounds of formula (VI) may be prepared by reacting the compounds of formula (VII)

(VII)

with benzaldehyde under suitable condensation conditions. For example the reaction conveniently takes place in the presence of a suitable solvent such as an alcohol (e.g. ethanol) in the presence of a base such as sodium hydroxide and at an elevated temperature e.g. the reflux temperature of the reaction mixture.

The ketone of formula (VII) is known (L. J. Street et al., *J.Med.Chem.*, 1990, 33, 2690).

The amines of formula (IV) may be prepared by reductive amination of the ketone of formula (II) with ammonium acetate in the presence of sodium cyanoborohydride. Alternatively the ketones of formula (II) may be reacted with a suitable oximating agent such as hydroxylamine hydrochloride to give the corresponding oxime which is in turn reduced to the amine of formula (IV) using a suitable reducing agent e.g. lithium aluminum hydride or by catalytic hydrogenation for example palladium as catalyst.

The amines of formula (IV) may also be prepared from the N-benzyl analogues of formula (VIII)

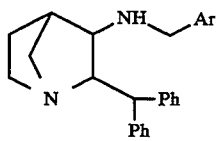

(VIII)

(where Ar represents an optionally substituted phenyl ring such as p-methoxyphenyl) by removing the benzyl substituent, for example, when Ar represents p-methoxyphenyl, the benzyl substituent may be removed using hydrobromic acid or, when Ar is unsubstituted, the benzyl group may be removed by catalytic hydrogenation for example using palladium as catalyst.

Compounds of formula (VIII) may be prepared by reacting the ketone of formula (II) with $NH_2$—$CH_2Ar$ (where Ar is defined as above) under the conditions described for process (A) above.

The intermediates of formulae (II), (IV), (VI) and (VIII) are novel compounds and thus form a further feature of the invention.

Where it is desired to isolate a compound formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester ( e.g. ethyl acetate ) or an ether (e.g. tetrahydrofuran).

Pharmaceutically acceptable salts may also be prepared from other salts, including other pharmaceutically acceptable salts, of the compound of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, in one example an appropriate optically active acid may be used; to form salts with the enantiomeric mixture of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of general formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which can then be separated by conventional means e.g. by chromatography or by fractional crystallisation. Alternatively, the diastereoisomers may be separable without the need for further derivatization.

Standard resolving methods are described for example in 'Stereochemistry of Carbon Compounds' by E. L. Eliel (McGraw Hill, 1962) and 'Tables of Resolving Agents' by S. H. Wilen.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples which are not intended as a limitation of the invention. All temperatures are in °C. Thin layer chromatography (t.l.c.) was carried out on silica, flash column chromatography (FCC) on silica (Merck 9385), and short path chromatography (SPC) on silica (Merck 7729). The following abbreviations are used: ether-diethyl ether; System A—ethyl acetate/methanol/ammonia; System B—petroleum ether/ethyl acetate/methanol/ammonia.

Intermediate 1

2-(Phenylmethylene)-1-azabicyclo[2.2.1]heptan-3-one

A mixture of 1-azabicyclo [2.2.1] heptan-3-one (2.65 g), benzaldehyde (3.64 ml) and sodium hydroxide (1.15 g) in ethanol (25 ml) was heated at reflux for 40 min. After cooling the solvent was removed in vacuo and the residue partitioned between dichloromethane (300 ml) and water (300 ml). The aqueous layer was further extracted with dichloromethane (2×300 ml). The organic extracts were combined, backwashed with brine (100 ml), dried and concentrated in vacuo to give an orange oil (5.84 g). The oil was purified by FCC, using gradient elution with petrol/ethyl acetate 6:1 to 3:1 to give the title compound as a yellow solid (3.80 g). m.p. 61°–63°.

TLC (petrol/ethyl acetate, 3:1) Rf 0.39.

Intermediate 2

(endo)-2-(Diphenylmethyl)-1-azabicyclo[2.2.1]heptan-3-one(I) and (exo)-2-(Diphenylmethyl)-1-azabicyclo[2.2.1]heptan-3-one (II)

Phenyl magnesium bromide (1M solution in tetrahydrofuran, 37.84 ml) was added dropwise to an ice-bath cooled suspension of copper thiophenoxide (657 mg) in dry tetrahydrofuran (50 ml). The mixture was allowed to stir for 10 min then a solution of 2-(phenylmethylene)-1-azabicyclo [2.2.1] heptan-3-one (3.77 g) in dry tetrahydrofuran (50 ml) was added portionwise to the reaction mixture, which was allowed to warm to room temperature over 2 h. Saturated ammonium chloride (50 ml) was added slowly to the reaction which was then allowed to stir for 20 minutes. Saturated ammonium chloride (50 ml) and ether (150 ml) were added and the ether layer separated. The aqueous layer was further extracted with ether (2×150 ml) and the combined organic extracts were backwashed with brine (2×50 ml), dried and concentrated in vacuo to give an orange oil (7.36 g). The oil was purified by FCC, eluting with System B (30:70:0.5:0.1) to System A (100:0.5:0.1) to give isomer I as a white solid (2.38 g), and isomer II as a pale yellow solid (752 mg).

TLC (System A, 100:2:0.1) Rf 0.30 isomer I Rf 0.61 isomer II

EXAMPLE 1

(exo, exo)-2-(Diphenylmethyl)-N-[(2-methoxyphenyl)methyl]-1-azabicyclo [2.2.1]heptan-3-amine To a solution of (exo-2-(diphenylmethyl-1-azabicyclo[2.2.1]heptan-3-one (50 mg) in dry toluene (15 ml) was added 2 -methoxybenzylamine (0.035 ml) and para-toluenesulphonic acid (10 mg). The mixture was heated at reflux in a Dean-Stark water separator for 22 h. The solvent was removed in vacuo and the residue dissolved in dry tetrahydrofuran (15 ml). A solution of 9-borabicyclononane in tetrahydrofuran (0.5M, 0.72 ml) was added and the reaction mixture was allowed to stir under nitrogen for 5 h. A further amount of the 9-borabicyclononane solution (0.72 ml) was added and stirring was continued for 20 h. 2N Sodium hydroxide (10 ml) was added to the reaction mixture and after stirring for 40 min the organic solvent was removed in vacuo, and the residue was extracted with ethyl acetate (3×25 ml). The combined organic extracts were back-washed with brine (10 ml), dried and concentrated in vacuo to a yellow oil (242 mg). The oil was purified by SPC, eluting with System A (100:4:0.5) to give the title compound as a pale yellow solid (35 mg). m.p. 142°–144°.

TLC (System A, 100:10:0.5) Rf 0.38

EXAMPLE 2

(endo,endo)-2-(Diphenylmethyl)-N-[(2-methoxyphenyl)methyl]-1-azabicyclo[2.2.1]heptan-3-amine hydrochloride To a solution of (endo-2-(diphenylmethyl)-1-azabicyclo[2.2.1]heptan-3-one (500 mg) in dry dichloromethane (50 ml) was added 2-methoxybenzylamine (2.7 mmol) and activated 4A molecular sieves. The reaction mixture was allowed to stir at room temperature under nitrogen for 21 h. Para-toluenesulphonic acid (50 mg) was added, and stirring was continued for 4 h after which time ethanol (50 ml) was added to the reaction mixture, followed by sodium borohydride (341 mg). The reaction mixture was allowed to stir for 48 h, filtered and then water (5 ml) was added to the filtrate. The organic solvent was removed in vacuo and water (300 ml) added to the residue which was extracted with dichloromethane (3×200 ml). The combined organic extracts were washed with brine, dried and the solvent removed in vacuo to give a yellow solid (1.0 g). The solid was purified by SPC, eluting with System A (100:10:0.5) to give a white foam (112 mg) which was converted into the hydrochloride salt to give the title compound as a white solid (13.2 mg), m.p. 174°–6°.

TLC (System A, 100:10:0.5) Rf 0.28

EXAMPLE 3

(exo, endo)-2-(Diphenylmethyl)-N-[(5-fluoro-2-methoxyphenyl)methyl]-1-azabicyclo[2.2.1]heptan-3-amine dihydrochloride A mixture of (exo, endo)-2-(diphenylmethyl)-1-azabicyclo[2.2.1]heptan-3-one (500 mg), 4-toluenesulphonic acid (70.0 mg) and 5-fluoro-2-methoxy benzylamine (420 mg) in anhydrous toluene (20 ml) was heated under reflux with stirring in a Dean-Stark water separator for 18 h. Upon cooling to room temperature, the solvent was evaporated in vacuo and the residue was dissolved in anhydrous tetrahydrofuran (7 ml) and cooled to 0°. A solution of 9-borabicyclononane in tetrahydrofuran (7.2 ml of 0.5M) was added, and stirring was continued at room temperature for 48 h. The solvent was evaporated in vacuo and the residue was diluted with 2M aqueous sodium hydroxide solution (30 ml) and extracted with ethyl acetate (3×20 ml). The combined organic extracts were washed with brine (1×10 ml), dried and concentrated in vacuo to leave a yellow oil. The oil was purified by column chromatography on silica (Merck HF254) eluting with a mixture of ethyl acetate and methanol (containing 5% $NH_3$) (95:5) to give two fractions, which were treated with etheral hydrogen chloride to give the title compound (160 mg) as a white solid, m.p. 162°–164°.

TLC (5% methanol/ammonia:ethyl acetate, 5:95) Rf 0.2(5)and also

EXAMPLE 4

(exo, exo)-2-(Diphenylmethyl)-N-[(5-fluoro-2-methoxyphenyl)methyl]-1-azabicyclo[2.2.1]heptan-3-amine dihydrochloride (100 mg) as a white solid, m.p. 168°–170°.

TLC (5% methanol/ammonia:ethyl acetate, 5:95) Rf 0.2(0)

EXAMPLE 5

(endo,endo)-2-(Diphenylmethyl)-N-[2-pyridylmethyl]-1-azabicyclo[2.2.1]heptan-3-amine hydrochloride To a solution of (endo)-2-(diphenylmethyl)-1-azabicyclo[2.2.1]heptan-3-one (250 mg) and 2-aminomethylpyridine (102 μl) in dichloroethane (20 ml) was added sodium triacetoxyborohydride (286 mg), followed by acetic acid (57 μl), and the reaction stirred for 48 h. The reaction mixture was diluted with dichloromethane (30 ml) and washed successively with saturated sodium bicarbonate solution (2×50 ml), water (50 ml) and brine (50 ml). The organic solution was dried, and evaporated to a gum. FCC, eluting with System A (75:25:1) gave a gum (170 mg) which was converted to the hydrochloride salt with methanolic hydrochloric acid to give the title compound (196 mg) as a white solid.

m.p. 170°–172° (decomp)

T.l.c. (System A 75:25:1) Rf 0.34.

EXAMPLE 6

(endo,endo)-2-(Diphenylmethyl)-N-[(2-methylthiophenyl)methyl]-1-azabicyclo[2.2.1]heptan-3-amine hydrochloride a mixture of (endo)-2-(diphenylmethyl)-1-azabicyclo[2.2.1]heptan-3-one (100 mg), 2-methylthiobenzylamine (83 mg), paratoluenesulphonic acid (205 mg) acid 4 A molecular sieves (2 g) were stirred in methanol (10 mls) for 3 h. Sodium cyanoborohydride (113 mg) was added, and the reaction mixture was stirred for 48 h. The mixture was filtered, and the filtrate concentrated to dryness. The residue was partitioned between ethyl acetate (50 ml) and saturated sodium bicarbonate solution (50 ml), the organic layer washed with water (2×50 ml) and brine (50 ml), dried, and concentrated in vacuo to give a yellow oil. FCC eluting with System A (100:10:0.5) gave a gum (39 mg) which was converted to the hydrochloride salt with methanolic hydrochloric acid to give the title compound (44 mg) as a pale yellow solid.

m.p. 168°–70° (decomp)
T.l.c. (System A: 100:10:1) Rf 0.58

Biological Data

The anti-emetic activity of the test compound (±) cis-3-(2-methoxybenzylamino)-2-phenyl piperidine was demonstrated by its ability to inhibit cisplatin-induced emesis in the ferrett.

In this model of emesis the onset of retching and vomiting occurs approximately 1 hour after the administration of cisplatin (200 mg/m² i.p.). At the first retch in response to cisplatin, the test compound was administered (e.g. i.p., p.o., i.v., s.c., i.c.v.) and its effect on emesis determined by comparison with appropriate controls (e.g. water).

The test compound exhibited anti-emetic activity when administered at a dose of 3 mg/kg i.p.

The above test compound (3 mg/kg i.p) also exhibited anti-emetic activity following simultaneous administration with the emetogens cyclophosphamide (200 mg/kg i.p) , morphine (0.5 mg/kg s.c), ipecacuanha (2 mg/kg p.o) and copper sulphate (40 mg/kg i.p.).

The (2S,3 S) enantiomer of the test compound cis-3-(2-methoxybenzylamino)-2-phenyl piperidine inhibited cisplatin-induced emesis in the ferrett when administered at a dose of 3 mg/kg i.p. The (2R,3 R) enantiomer of the above test compound, which is 1000-fold less active as an $NK_1$ receptor antagonist than the (2S,3 S) enantiomer, was inactive in the above emesis test.

The compound of formula (I) (exo,exo)-2-(diphenylmethyl)-N-[(2-methoxyphenyl)methyl]-1-azabicyclo [2.2.1] heptan-3-amine (Example 1) also inhibited cisplatin-induced emesis in the ferrett when administered at a dose of 5 mg/kg i.p.

The test compound N-[N¹-[L-pyroglutamyl-L-alanyl-L-aspartyl-L-prolyl-L-asparaginyl-L-lysyl-L-phenylalanyl-L-tyrosyl]-4-methyl-1-oxo-2S-(6-oxo-5S-1,7-diazaspiro[4.4]nonan-7-yl)pentyl]-L-tryptophanamide also inhibited cisplatin-induced emesis in the ferret when administered at a dose of 10 mg i.c.v.

We claim:

1. A method for the treatment of a mammal, suffering from emesis, wherein said emesis is induced by cancer chemotherapeutic agents, radiation sickness, radiation therapy, poisons, toxins, post-operative sickness or opioid analgesics, comprising administration of an effective amount of an $NK_1$ receptor antagonist of formula H, V' or W:

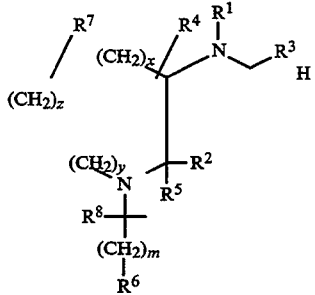

wherein in the antagonist of formula H:
x is an integer from zero to four;
y is an integer from zero to four;
z is an integer from one to six;
the ring containing $(CH_2)_z$ may contain from zero to three double bonds, and one of the carbons of $(CH_2)_z$ may optionally be replaced by oxygen, sulfur or nitrogen;
m is an integer from zero to twelve, and any one of the carbon-carbon single bonds of $(CH_2)_m$ may optionally be replaced by a carbon-carbon double or triple bond and any one of the carbon atoms of $(CH_2)_m$ may optionally be substituted with $R^8$;
$R^1$ is hydrogen or $(C_{1-6})$alkyl optionally substituted with hydroxy, alkoxy or fluoro;
$R^2$ is a radical selected from the group consisting of hydrogen, $(C_{1-6})$ straight or branched alkyl, $(C_{3-7})$cycloalkyl wherein one of the carbon atoms may optionally be replaced by nitrogen, oxygen or sulfur; aryl selected from the group consisting of phenyl and naphthyl; heteroaryl selected from the group consisting of indanyl, thienyl, furyl, pyridyl, thiazolyl, isothiazolyl, oxazolyl, isoxazolyl, triazolyl, tetrazolyl and quinolyl; phenyl$(C_{2-6})$alkyl, benzhydryl and benzyl, wherein each of said aryl and heteroaryl groups and the phenyl moieties of said benzyl, phenyl$(C_{2-6})$alkyl and benzhydryl groups may optionally be substituted with one or more substituents independently selected from the group consisting of halo, nitro, $(C_{1-6})$alkoxy, trifluoromethyl, amino, $(C_{1-6})$alkylamino, $(C_{1-6})$alkyl-O—C(O), $(C_{1-6})$alkyl-O—C(O)$(C_{1-6})$alkyl-CO$_2$—, $(C_{1-6})$alkyl-C(O)-$(C_{1-6})$alkyl-O—, $(C_{1-6})$alkyl-C(O)—, $(C_{1-6})$alkyl-C(O)-$(C_{1-6})$alkyl-, di-$(C_{1-6})$alkylamino, —CONH-$(C_{1-6})$alkyl, $(C_{1-6})$alkyl-CONH-$(C_{1-6})$alkyl, —NHC(O)H and —NH-C(O)$(C_{1-6})$alkyl;
$R^5$ is hydrogen or $(C_{1-6})$alkyl; or
$R^2$ and $R^5$, together with the carbon to which they are attached, form a saturated carbocyclic ring having from 3 to 7 carbon atoms, wherein one of said carbon atoms may optionally be replaced by oxygen, nitrogen or sulfur;
$R^3$ is aryl selected from the group consisting of phenyl and naphthyl; heteroaryl selected from the group consisting of indanyl, thienyl, furyl, pyridyl, thiazolyl, isothiazolyl, oxazolyl, isoxazolyl, triazolyl, tetrazolyl and quinolyl; or cycloalkyl having from three to seven carbon atoms, wherein one of said carbon atoms may optionally be replaced by nitrogen, oxygen or sulfur; wherein each of said aryl and heteroaryl groups may optionally be substituted with one or more substituents and said $(C_{3-7})$cycloalkyl may optionally be substituted with one or two substituents, said substituents being independently selected from the group consisting of halo, nitro, $(C_{1-6})$alkyl, $(C_{1-6})$alkoxy, trifluoromethyl, amino, phenyl, $(C_{1-6})$alkylamino, —CONH-$(C_{1-6})$alkyl, $(C_{1-6})$alkyl-CONH-$(C_{1-6})$alkyl, —NHC(O)H and —NHC(O)-$(C_{1-6})$alkyl;
$R^4$ may be attached to any atom of the nitrogen containing ring having an available bonding site and $R^7$ may be attached to any atom of the $(CH_2)_z$ containing ring having an available bonding site;
$R^4$, $R^6$, $R^7$ and $R^8$ are each independently selected from the group consisting of hydrogen, hydroxy, halo, amino, carboxy, carboxyalkyl, $(C_{1-6})$alkylamino, di-$(C_{1-6})$alkylamino, $(C_{1-6})$alkoxy, $(C_{1-6})$alkyl-O—C(O)—, $(C_{1-6})$alkyl-O—C(O)-$(C_{1-6})$alkyl, $(C_{1-6})$alkyl-CO$_2$, $(C_{1-6})$alkyl-C(O)-$(C_{1-6})$alkyl-O-$(C_{1-6})$alkyl-C(O)—, $(C_{1-6})$alkyl-C(O)$(C_{1-6})$alkyl, and the radicals set forth in the definition of $R^2$, with the proviso that (a) when m is 0, $R^8$ is absent, (b) neither $R^4$, $R^6$, $R^7$ nor $R^8$ can form, together with the carbon to which it is attached, a ring with $R^5$, and (c) $R^4$ and $R^7$ can not be attached to the same carbon atom;

or a pharmaceutically acceptable salt thereof;

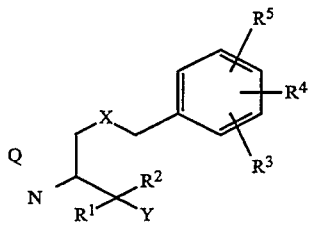

wherein in the antagonist of formula V':

Q is the residue of an optionally substituted azabicyclic ring system;

X represents oxa or thia;

Y represents H or hydroxy;

$R^1$ and $R^2$ independently represent phenyl or thienyl, either of which groups may be optionally substituted by halo or trifluoromethyl;

$R^3$, $R^4$ and $R^5$ independently represent H, $(C_{1-6})$alkyl, $(C_{2-6})$alkenyl, $(C_{2-6})$alkynyl, halo, cyano, nitro, trifluoromethyl, trimethylsilyl, -$OR^a$, $SCH_3$, $SOCH_3$, $SO_2CH_3$, —$NR^aR^b$, $NR^aCOR^b$, $NR^a$-$CO_2R^b$, —$CO_2R^a$ or —$CONR^aR^b$; and $R^a$ and $R^b$ independently represent H, $(C_{1-6})$alkyl, phenyl or trifluoromethyl;

or a salt or prodrug thereof;

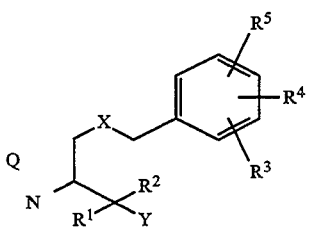

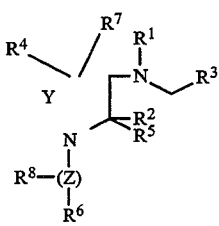

wherein in the antagonist of formula W:

Y is $(CH_2)_n$ wherein n is an integer from 1 to 4, and wherein any one of the carbon-carbon single bonds in $(CH_2)_n$ may optionally be replaced by a carbon-carbon double bond, and wherein any one of the carbon atoms of $(CH_2)_n$ may optionally be substituted with $R^4$ and wherein any one of the carbon atoms of $(CH_2)_n$ may optionally be substituted with $R^7$;

Z is $(CH_2)_m$, wherein m is an integer from 0 to 6, and wherein any one of the carbon-carbon single bonds of $(CH_2)_m$ may optionally be replaced by a carbon-carbon double bond or carbon-carbon triple bond, and any one of the carbon atoms of $(CH_2)_m$ may optionally be substituted with $R^8$;

$R^1$ is hydrogen or $(C_{1-8})$alkyl optionally substituted with hydroxy, $(C_{1-4})$alkoxy or fluoro;

$R^2$ is a radical selected from the group consisting of hydrogen, $(C_{1-6})$ straight or branched alkyl, $(C_{3-7})$cycloalkyl wherein one of the $CH_2$ groups in said cycloalkyl may optionally be replaced by NH, oxygen or sulfur; aryl selected from the group consisting of phenyl and naphthyl; heteroaryl selected from the group consisting of indanyl, thienyl, furyl, pyridyl, thiazolyl, isothiazolyl, oxazolyl, isoxazolyl, triazolyl, tetrazolyl and quinolyl; phenyl-$(C_{2-6})$-alkyl, benzhydryl and benzyl, wherein each of said aryl and heteroaryl groups and the phenyl moieties of said benzyl, phenyl-$(C_{2-6})$-alkyl and benzhydryl may optionally be substituted with one or more substituents independently selected from the group consisting of halo, nitro, $(C_{1-6})$alkyl, $(C_{1-6})$alkoxy, trifluoromethyl, amino, $(C_{1-6})$alkylamino, $(C_{1-6})$alkyl-O—C(O)—, $(C_{1-6})$alkyl-O—C(O)-$(C_{1-6})$alkyl, $(C_{1-6})$alkyl-C(O)—O—, $(C_{1-6})$alkyl-C(O)-$(C_{1-6})$alkyl-O—, $(C_{1-6})$alkyl-C(O)—, $(C_{1-6})$alkyl-C(O)-$(C_{1-6})$alkyl-, di-$(C_{1-6})$alkylamino, —CONH-$(C_{1-6})$alkyl, $(C_{1-6})$alkyl-CONH-$(C_{1-6})$alkyl, NHC(O)H and —NHC(O)-$(C_{1-6})$alkyl; and wherein one of the phenyl moieties of said benzhydryl may optionally be replaced by naphthyl, thienyl, furyl or pyridyl;

$R^5$ is hydrogen, phenyl or $(C_{1-6})$alkyl; or $R^2$ and $R^5$, together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from the group consisting of phenyl and naphthyl; heteroaryl selected from the group consisting of indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the $(CH_2)$ groups in said cycloalkyl may optionally be replaced by NH, oxygen or sulfur; wherein each of said aryl and heteroaryl groups may optionally be substituted with one or more substituents, and said $(C_{3-7})$ cycloalkyl may optionally be substituted with one or two substituents, each of said substituents being independently selected from the group consisting of halo, nitro, $(C_{1-6})$alkyl, $(C_{1-6})$alkoxy, trifluoromethyl, amino, $(C_{1-6})$alkylamino, —CONH-$(C_{1-6})$alkyl, $(C_{1-6})$alkyl-C(O)—NH-$(C_{1-6})$alkyl, —NHC(O)H and —NHC(O)-$(C_{1-6})$alkyl; and $R^4$ and $R^7$ each independently selected from the group consisting of hydroxy, hydrogen, halo, amino, oxo, cyano, methylene, hydroxymethyl, halomethyl, $(C_{1-6})$alkylamino, di$(C_{1-6})$alkylamino, $(C_{1-6})$alkoxy, $(C_{1-6})$alkyl-O—C(O)—, $(C_{1-6})$alkyl-O—C(O)-$(C_{1-6})$alkyl, $(C_{1-6})$alkyl-C(O), $(C_{1-6})$alkyl-C(O)-$(C_{1-6})$alkyl-O, $(C_{1-6})$alkyl-C(O), $(C_{1-6})$alkyl-C(O)-$(C_{1-6})$alkyl, and the radicals set forth in the definition of $R^2$;

$R^6$ is $NHC(O)R^9$, —$NHCH_2R^9$, $SO_2R^9$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $(C_{1-6})$alkyl, hydrogen, phenyl or phenyl$(C_{1-6})$alkyl;

with the proviso that (a) when m is O, $R^8$ is absent, (b) when $R^4$, $R^6$, $R^7$ or $R^8$ is defined in $R^2$, it cannot form, together with the carbon to which it is attached, a ring with $R^5$, and (c) when $R^4$ and $R^7$ are attached to the same carbon atom, then either each of $R^4$ and $R^7$ is independently selected from the group consisting of hydrogen, fluoro and ($C_{1-6}$)alkyl, or $R^4$ and $R^7$, together with the carbon to which they are attached, form a ($C_{3-6}$) saturated carbocyclic ring that forms a spiro compound with the nitrogen containing ring to which they are attached;

or a pharmaceutically acceptable acid addition salt thereof.

2. A method according to claim 1 wherein said emesis is induced by a cancer chemotherapeutic agent.

3. A method according to claim 2 wherein said cancer chematherapeutic agent is selected from cyclophosphamide, carmustine, lomustine, chloroambucil, dactinomycin, doxorubicin, mitomycin-C, bleomycin, cytarabine, methotrexate, 5-fluorouracil, etoposide, vinblastine, vincristine, cisplatin, dacarbazine, procarbazine, hydroxyurea, and combinations thereof.

4. A method according to claim 3 wherein said emesis is induced by cisplatin.

5. A method according to claim 3 wherein said emesis is induced by cyclophosphamide.

6. A method according to claim 1 wherein said emesis is induced by morphine, ipecacuanha or copper sulphate.

7. A method according to claim 1 wherein the NK, receptor antagonist is (2S,3S)-3-(2-methoxybenzylamino)-2-phenyl piperidine or a pharmaceutically acceptable acid addition salt thereof.

8. A method according to claim 1 wherein the $NK_1$ receptor antagonist is a compound of formula H or V':

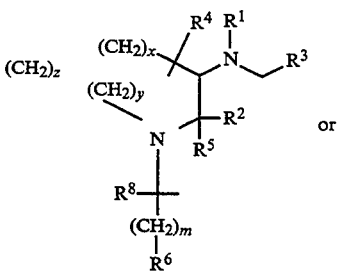

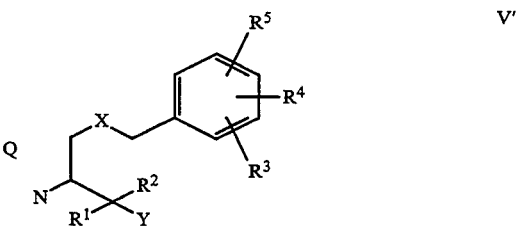

or a pharmaceutically acceptable acid addition salt thereof.

9. A method according to claim 1 wherein the $NK_1$ receptor antagonist is a compound of formula W

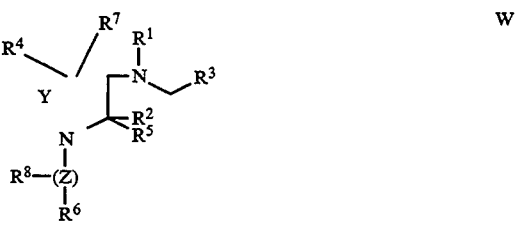

or a pharmaceutically acceptable acid addition salt thereof.

* * * * *

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 4:

Formula H should read:

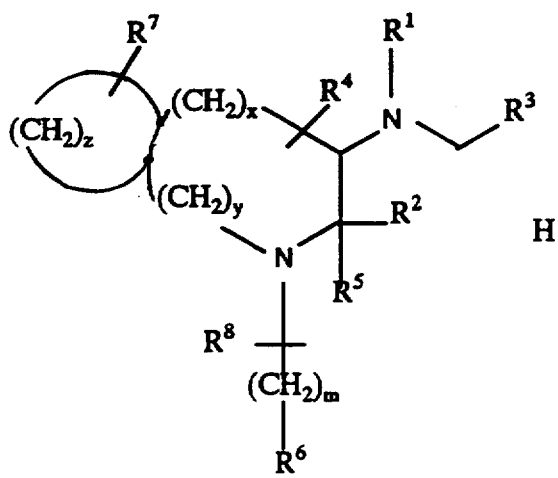

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 7:

Formula L should read:

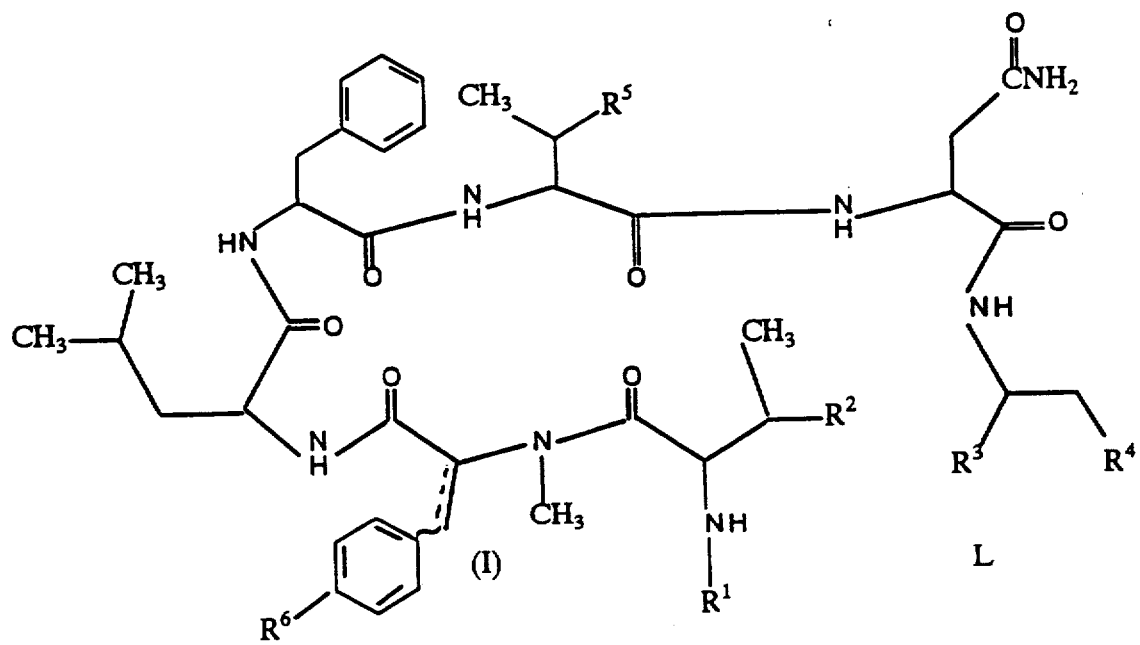

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 9:

Formula Q should read:

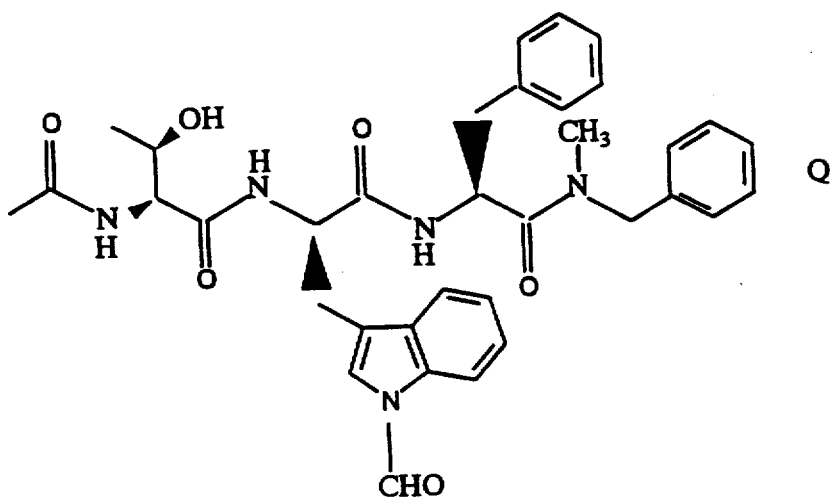

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 11:

Formula V' should read:

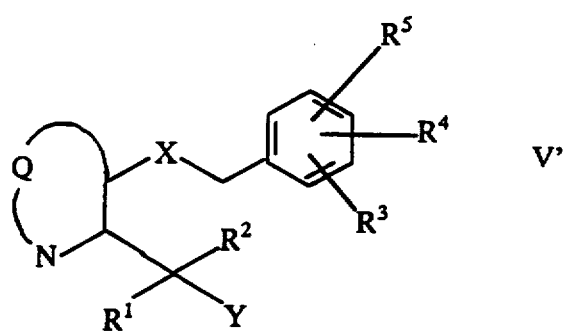

V'

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 11:

Formula W should read:

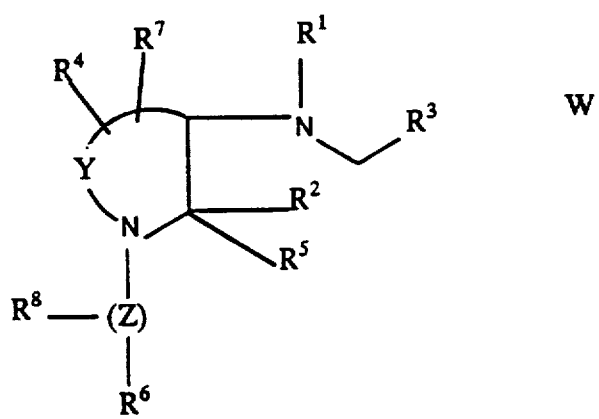

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 15:

Formulae (a), (b) and (c) should read:

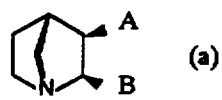 (a)   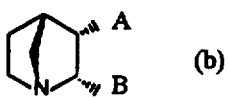 (b)

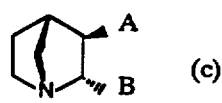 (c)

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 16:

Formula (d) should read:

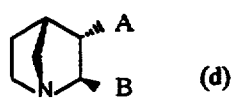

(d)

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 25:

Formula H should read:

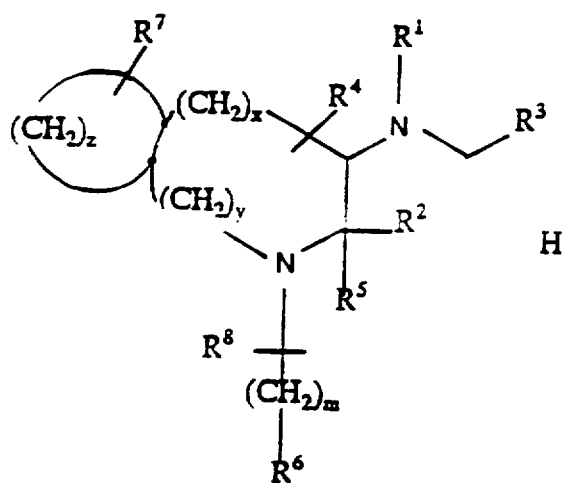

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 27:

Formula V' (first occurrence) should read:

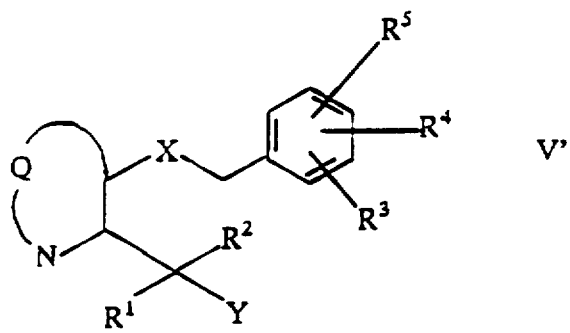

Lines 35-40, delete formula V' (second occcurence).

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 27:

Formula W should read:

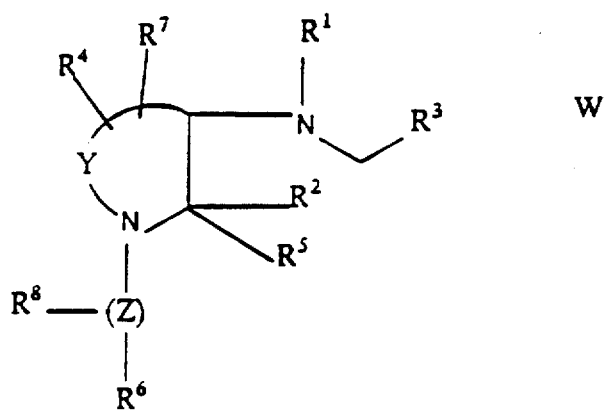

UNITED STATES PATENT AND TRADEMARK OFFICE
CERTIFICATE OF CORRECTION

PATENT NO. : 5,360,820

DATED : November 1, 1994

INVENTOR(S) : Russell M. HAGAN et al.

It is certified that error appears in the above-indentified patent and that said Letters Patent is hereby corrected as shown below:

COLUMN 29:

Line 33, "NK," should read --$NK_1$--.

COLUMN 30:

Formulae H and V' should read:

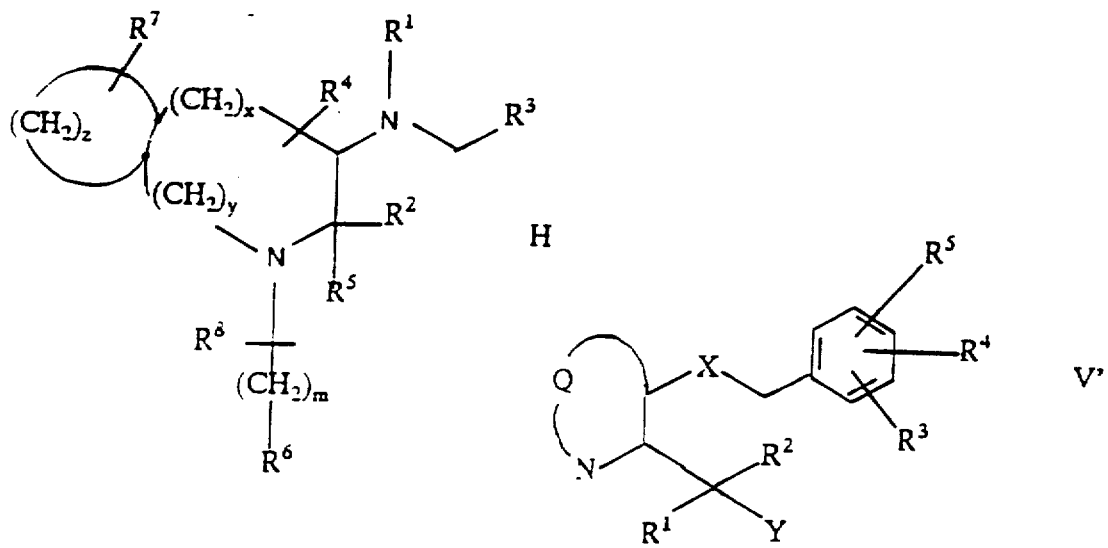

UNITED STATES PATENT AND TRADEMARK OFFICE
CERTIFICATE OF CORRECTION

PATENT NO. : 5,360,820
DATED : November 1, 1994
INVENTOR(S) : Russell M. Hagan et al It is certified that error appears in the above-indentified patent and that said Letters Patent is hereby corrected as shown below:

COLUMN 30:

Formula W should read:

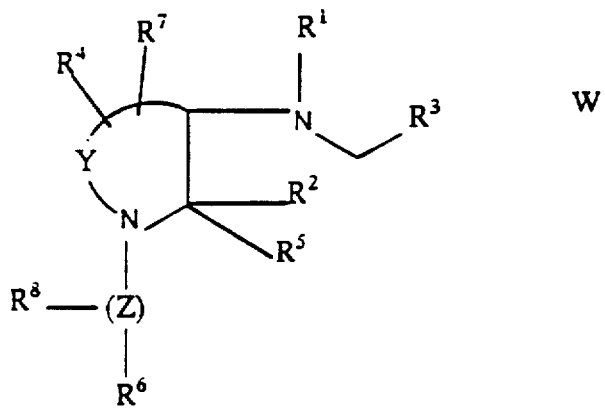

Signed and Sealed this

Eighteenth Day of April, 1995

Attest:

BRUCE LEHMAN

Attesting Officer

*Commissioner of Patents and Trademarks*

UNITED STATES PATENT AND TRADEMARK OFFICE
CERTIFICATE OF CORRECTION

PATENT NO. : 5,360,820
DATED : November 1, 1994
INVENTOR(S) : Russell M. HAGAN et al.

It is certified that error appears in the above-indentified patent and that said Letters Patent is hereby corrected as shown below:

On the title page:

ITEM [75] Inventors:

Change Russell M. Hagan; Keith T. Bunce; Alan Naylor, Mark Ladlow, all of Ware, Great Britain; Andrew B. McElroy, Research Triangle Park,

N.C.; Andrew R. Whittington; Barry A. Coomber, both of Greenford,

Great Britain to Russell M. Hagan; Keith T. Bunce, both of Ware, Great Britain Signed and Sealed this Thirty-first Day of December, 1996

*Attest:*

BRUCE LEHMAN

*Attesting Officer*  *Commissioner of Patents and Trademarks*